United States Patent
Patel et al.

(10) Patent No.: US 9,717,667 B2
(45) Date of Patent: Aug. 1, 2017

(54) ORAL CARE COMPOSITION CONTAINING IONIC LIQUIDS

(71) Applicant: Colgate-Palmolive Company, New York, NY (US)

(72) Inventors: Madhusudan Patel, Somerset, NJ (US); Guillaume Picquet, Long Valley, NJ (US); Mark Vandeven, Morristown, NJ (US); Mahmoud Hassan, Somerset, NJ (US); Rosa Paredes, North Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/654,417

(22) PCT Filed: Dec. 20, 2012

(86) PCT No.: PCT/US2012/070952
§ 371 (c)(1),
(2) Date: Jun. 19, 2015

(87) PCT Pub. No.: WO2014/098868
PCT Pub. Date: Jun. 26, 2014

(65) Prior Publication Data
US 2015/0335549 A1 Nov. 26, 2015

(51) Int. Cl.
| | |
|---|---|
| A61K 8/368 | (2006.01) |
| A61K 8/41 | (2006.01) |
| A61K 8/46 | (2006.01) |
| A61K 8/49 | (2006.01) |
| A61Q 11/00 | (2006.01) |
| A61K 45/06 | (2006.01) |
| A61K 31/095 | (2006.01) |
| A61K 31/14 | (2006.01) |
| A61K 31/60 | (2006.01) |

(52) U.S. Cl.
CPC ............. *A61K 8/416* (2013.01); *A61K 8/368* (2013.01); *A61K 8/466* (2013.01); *A61K 8/4926* (2013.01); *A61K 31/095* (2013.01); *A61K 31/14* (2013.01); *A61K 31/60* (2013.01); *A61K 45/06* (2013.01); *A61Q 11/00* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 3,235,459 A | 2/1966 | Francis | |
| 3,257,276 A * | 6/1966 | Broh-Kahn | A61K 9/006 514/159 |
| 3,576,873 A | 4/1971 | Crounse | |
| 4,256,730 A * | 3/1981 | Benedict | A61Q 11/00 424/49 |
| 4,256,731 A | 3/1981 | Curtis et al. | |
| 4,273,759 A | 6/1981 | Gaffar et al. | |
| 4,820,507 A | 4/1989 | Klueppel et al. | |
| 5,415,813 A * | 5/1995 | Misselyn | C11D 1/83 510/108 |
| 7,087,190 B2 * | 8/2006 | Hei | A01N 59/00 252/187.21 |
| 7,939,485 B2 | 5/2011 | Price et al. | |
| 2005/0019275 A1 | 1/2005 | Sagel et al. | |
| 2005/0118261 A1 * | 6/2005 | Oien | A61K 9/0014 424/468 |
| 2006/0090777 A1 | 5/2006 | Hecht et al. | |
| 2006/0094617 A1 | 5/2006 | Price et al. | |
| 2007/0054834 A1 * | 3/2007 | Baker | A61K 31/14 510/504 |
| 2010/0016205 A1 | 1/2010 | Schwab | |
| 2010/0055053 A1 * | 3/2010 | Ripley | A61K 8/365 424/49 |
| 2011/0091538 A1 * | 4/2011 | Geshuri | A61K 6/0008 424/452 |
| 2014/0083465 A1 | 3/2014 | D'Ambrogio et al. | |

FOREIGN PATENT DOCUMENTS

| | | |
|---|---|---|
| EP | 0150374 | 4/1991 |
| EP | 1296650 | 3/2005 |

(Continued)

OTHER PUBLICATIONS

Darby and Walsh (Dental Hygiene Theory and Practice, Fourth Edition, 2016, p. 86).*

(Continued)

*Primary Examiner* — Alma Pipic

(57) ABSTRACT

An oral care composition is provided wherein the composition comprises an ionic liquid, wherein the ionic liquid comprises: a) a quaternary ammonium cation of the formula wherein $R_1$, $R_2$, $R_3$ and $R_4$ are each an organic moiety and may be the same or different, and at least one of $R_1$, $R_2$, $R_3$ and $R_4$ includes a hydroxyl; and b) an anion selected from the group consisting of salicylate, alkylsulfate, sulfate, acetate, halide, phosphate, alkyl phosphate and tosylate; wherein the oral care composition is a mouth rinse, toothpaste, toothpowder, oral bead or strip, fluid-encased dental strip, irrigation fluid, plaque removal liquid, dental floss, hard candy, soft candy, lozenge, chewing gum, or lollipop.

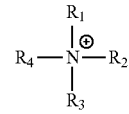

14 Claims, No Drawings

(56) References Cited

FOREIGN PATENT DOCUMENTS

| | | |
|---|---|---|
| FR | 2777459 | 10/1999 |
| GB | 1468557 | * 3/1977 |
| GB | 1468557 | 3/1997 |
| WO | WO 92/18096 | 10/1992 |
| WO | WO 93/11741 | 6/1993 |
| WO | WO 95/17159 | 6/1995 |
| WO | WO 97/02273 | 1/1997 |
| WO | WO 2004/003120 | 1/2004 |
| WO | WO 2005/123023 | 12/2005 |
| WO | WO 2006/131234 | 12/2006 |
| WO | WO 2011/087621 | 7/2011 |
| WO | WO 2012/177277 | 12/2012 |
| WO | WO 2013/052117 | 4/2013 |
| WO | WO 2014/098867 | 6/2014 |
| WO | WO 2014/098869 | 6/2014 |

OTHER PUBLICATIONS

Anonymous, 2012, "Bonjela" web page http://en.wikipedia.org/wiki/Bonjela, last modified date Oct. 12, 2012.
International Search Report and Written Opinion in International Application No. PCT/US2012/070952, mailed Oct. 8, 2013.
Written Opinion in International Application No. PCT/US2012/070952, mailed Mar. 5, 2015.

* cited by examiner

ORAL CARE COMPOSITION CONTAINING IONIC LIQUIDS

BACKGROUND OF THE INVENTION

An ionic liquid is a class of salt comprising a cation and an anion that is in liquid at a temperature of 100° C. or less and commonly have melting points below room temperature. While not wishing to be bound by theory, ionic liquids generally have much lower symmetry than conventional salts and the charge of cation and anion is distributed over a larger volume of the molecule by resonance in ionic liquids which is thought to contribute to their liquid state at much lower temperatures than conventional salts (e.g. NaCl, mp 801° C.). Ionic liquids are often composed of a cation comprising a heterocyclic ring and a counter anion, often inorganic in nature. The nature of the cation and anion will determine the hydrophobicity, viscosity, density and other physical parameters and properties of the ionic liquid.

Ionic liquids have been evaluated as environmentally-friendly or "green" alternatives to conventional organic solvents for a wide range of organic synthetic applications. Ionic liquids have unique characteristics that distinguish them from conventional organic solvents. For example, ionic liquids are non-volatile (i.e. they do not evaporate readily into the atmosphere), they have a high polarity and charge density, they may be hydrophobic or hydrophilic, and they have unique solvating properties. As such, ionic liquids are known to be used in cleaning compositions (for example as disclosed in US 2006/0090777 A1 and U.S. Pat. No. 7,939,485 B2). A range of ionic liquids are commercially available, or they may be readily synthesized by simple ion-exchange reactions.

A biofilm is a structured group of microorganisms encapsulated within a self-developed polymeric extracellular matrix. Biofilms are typically adhered to a living or inert surface. In the human or animal body biofilms can form on any internal or external surface. Biofilms have been found to be involved in a wide variety of microbial infections in the body and cause a number of conditions including urinary tract infections, middle-ear infections, and in particular diseases of the oral cavity.

Dental plaque is formed from a biofilm precursor, and is present to some degree on virtually all dental surfaces including dental instruments used by dental professionals. It comprises a dense microbial layer consisting of a mass of microorganisms embedded in a polysaccharide matrix. Plaque may form on any part of the tooth surface, and is found particularly at the gingival margin, and in cracks in the enamel. The danger associated with the formation of plaque on the teeth lies in the tendency of plaque to build up and eventually produce gingivitis, periodontitis and other types of periodontal disease, as well as dental caries and dental calculus. Dental plaque formation is also related to the feeling of a fuzzy tongue in an unclean oral cavity and as such addressing dental plaque formation can address cleaning the tongue.

Plaque itself adheres very firmly to dental surfaces and rapidly reforms on the tooth surface after it is removed. Current plaque removal methods rely primarily on the mechanical removal of plaque. These methods, which include brushing, brushing with an abrasive toothpaste, flossing, using interdental cleaners, scraping, using sonic energy (e.g. Sonicare toothbrushes) and ultrasound (e.g. Ultreo toothbrushes), in part, rely on a good brushing or flossing technique which many consumers simply do not possess. Moreover, these methods are particularly inefficient in removing stubborn plaque, or plaque hidden deep within cavities and fissures of teeth, or within gum pockets.

It is also known in the art to incorporate antimicrobial agents in oral compositions which destroy or retard the growth of bacteria. However, bacteria present in a biofilm or plaque deposit exhibit increased resistance to antimicrobial agents because the dense extracellular matrix and the outer layer of cells protect the bacteria found in the interior of the deposit from the effects of the antimicrobial agents.

There is therefore the need to provide improved methods and compositions for removing plaque which mitigate some of the inefficiencies resulting from a poor brushing/flossing technique and which effectively remove plaque hidden between teeth, within cavities and fissures of teeth, and in gum pockets.

SUMMARY OF THE INVENTION

The present invention aims at least partially to meet these needs in the art.

A first aspect of the present invention provides an oral care composition comprising an ionic liquid, wherein the ionic liquid comprises:

a) a quaternary ammonium cation of the formula

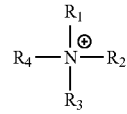

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate;

wherein the oral care composition is a mouth rinse, toothpaste, toothpowder, oral bead or strip, fluid-encased dental strip, irrigation fluid, plaque removal liquid, dental floss, hard candy, soft candy, lozenge, chewing gum, patch (e.g. intra oral patch similar to smokeless tobacco pouches) or lollipop.

Optionally, $R_1$, $R_2$, $R_3$ and $R_4$ are independently selected from substituted or unsubstituted alkyl and alkenyl moieties.

Optionally, at least one of $R_1$, $R_2$, $R_3$ and $R_4$ is a hydroxyalkyl group.

Optionally, one of $R_1$, $R_2$, $R_3$ and $R_4$ is a hydroxyalkyl group and three of $R_1$, $R_2$, $R_3$ and $R_4$ are substituted or unsubstituted alkyl groups.

Optionally, two of $R_1$, $R_2$, $R_3$ and $R_4$ are hydroxyalkyl groups and two of $R_1$, $R_2$, $R_3$ and $R_4$ are substituted or unsubstituted alkyl groups.

Optionally, three of $R_1$, $R_2$, $R_3$ and $R_4$ are hydroxyalkyl groups and one of $R_1$, $R_2$, $R_3$ and $R_4$ is a substituted or unsubstituted alkyl group.

Optionally, the hydroxyalkyl group is a $C_1$-$C_6$ hydroxyalkyl group.

Optionally, the hydroxyalkyl group is a $C_1$-$C_4$ hydroxyalkyl group.

Optionally, the hydroxyalkyl group is a hydroxyethyl group.

Optionally, the hydroxyalkyl group is a hydroxymethyl group.

Optionally, the alkyl group is a substituted or unsubstituted $C_1$-$C_6$ alkyl group.

Optionally, the alkyl group is a substituted or unsubstituted $C_1$-$C_4$ alkyl group.

Optionally, the alkyl group is an ethyl group.

Optionally, the alkyl group is a methyl group.

Optionally, the alkenyl group is a $C_2$-$C_6$ alkenyl group.

Optionally, the quaternary ammonium cation is choline or tris-(2-hydroxyethyl) methylammonium.

Optionally, the halide ion is a chloride ion or a bromide ion.

Optionally, the alkylsulfate or alkyl phosphate comprises from 1 to 22 carbon atoms, optionally from 1 to 4 carbon atoms, or 6 to 10 carbon atoms or 12 to 22 carbon atoms Optionally, the anion is selected from methylsulfate and salicylate.

Optionally, the ionic liquid is selected from the group consisting of choline salicylate, tris-(2-hydroxyethyl) methylammonium methylsulfate and mixtures thereof.

Optionally, the ionic liquid is choline salicylate.

Optionally, the ionic liquid is tris-(2-hydroxyethyl) methylammonium methylsulfate.

Optionally, the ionic liquid is present in the oral care composition in an amount of about 0.1 wt % to about 30 wt % based on the total weight of the composition.

Optionally, the ionic liquid is present in the oral care composition in an amount of about 0.5 wt % to about 20 wt % based on the total weight of the composition.

Optionally, the ionic liquid is present in the oral care composition in an amount of about 5 wt % to about 15 wt % based on the total weight of the composition.

Optionally, the ionic liquid is present in the oral care composition in an amount of about 8 wt % to about 10 wt % based on the total weight of the composition.

Optionally, the ionic liquid is present in the oral care composition at a concentration of about 1 mM to about 500 mM.

Optionally, the ionic liquid is present in the oral care composition at a concentration of about 5 mM to about 300 mM.

Optionally, the ionic liquid is present in the oral care composition at a concentration of about 15 mM to about 250 mM or 1 mM to 50 mM.

Optionally, the oral care composition comprises an abrasive in an amount of less than 0.1 wt % based on the total weight of the composition.

Optionally, the oral care composition comprises an abrasive in an amount of less than 0.01 wt % based on the total weight of the composition Optionally the composition is substantially free of any abrasives.

Optionally, the composition further comprises one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, abrasives and mixtures thereof.

Optionally, the composition comprises a surfactant selected from polysorbate 20, polysorbate 80, PEG 40, or a PEG-PPG-PEG block copolymer.

Optionally, the surfactant is present in the oral care composition in an amount of about 0.75 wt % to 1.5 wt % based on the total weight of the composition.

Optionally, the composition comprises a humectant selected from glycerin, sorbitol, propylene glycol and mixtures thereof.

Optionally, glycerin is present in an amount of about 0.1 wt % to about 15 wt %, sorbitol is present in an amount of about 0.1 wt % to about 20 wt % based on the total weight of the composition, and propylene glycol is present in an amount of about 0.1 wt % to about 7 wt % based on the total weight of the composition, based on the total weight of the composition.

Optionally, glycerin is present in an amount of about 15 wt % to about 40 wt %, sorbitol is present in an amount of about 20 wt % to about 40 wt % based on the total weight of the composition, and propylene glycol is present in an amount of about 10 wt % to about 40 wt % based on the total weight of the composition, based on the total weight of the composition.

Optionally, the antibacterial agent is cetyl pyridinium chloride (CPC).

Optionally, the composition is for removing or reducing plaque.

Optionally, the composition is for dissolving early morning salivary sediment.

Optionally, the composition is for disrupting and dissolving biofilm.

Optionally, the composition is for treating or preventing a disease or condition of the oral cavity.

Optionally, the disease or condition of the oral cavity is one or more of dental caries, tartar/calculus, erosion, gingivitis, periodontal disease, halitosis or xerostomia (dry mouth)

In a second aspect, the present invention provides a method of removing or reducing plaque from the oral cavity of a subject, comprising administering a therapeutically effective amount of a composition comprising at least one ionic liquid to the subject, wherein the ionic liquid comprises:

a) a quaternary ammonium cation of the formula

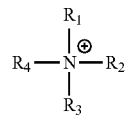

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

Optionally, $R_1$, $R_2$, $R_3$ and $R_4$ are independently selected from substituted or unsubstituted alkyl and alkenyl moieties.

Optionally, at least one of $R_1$, $R_2$, $R_3$ and $R_4$ is a hydroxyalkyl group.

Optionally, one of $R_1$, $R_2$, $R_3$ and $R_4$ is a hydroxyalkyl group and three of $R_1$, $R_2$, $R_3$ and $R_4$ are substituted or unsubstituted alkyl groups.

Optionally, two of $R_1$, $R_2$, $R_3$ and $R_4$ are hydroxyalkyl groups and two of $R_1$, $R_2$, $R_3$ and $R_4$ are substituted or unsubstituted alkyl groups.

Optionally, three of $R_1$, $R_2$, $R_3$ and $R_4$ are hydroxyalkyl groups and one of $R_1$, $R_2$, $R_3$ and $R_4$ is a substituted or unsubstituted alkyl group.

Optionally, the hydroxyalkyl group is a $C_1$-$C_6$ hydroxyalkyl group.

Optionally, the hydroxyalkyl group is a $C_1$-$C_4$ hydroxyalkyl group.

Optionally, the hydroxyalkyl group is a hydroxyethyl group.

Optionally, the hydroxyalkyl group is a hydroxymethyl group.

Optionally, the alkyl group is a substituted or unsubstituted $C_1$-$C_6$ alkyl group.

Optionally, the alkyl group is a substituted or unsubstituted $C_1$-$C_4$ alkyl group.

Optionally, the alkyl group is an ethyl group.

Optionally, the alkyl group is a methyl group.

Optionally, the alkenyl group is a $C_2$-$C_6$ alkenyl group.

Optionally, the quaternary ammonium cation is choline or tris-(2-hydroxyethyl) methylammonium.

Optionally, the halide ion is a chloride ion or a bromide ion.

Optionally, the alkylsulfate or alkyl phosphate comprises from 1 to 22 carbon atoms; optionally from 1 to 4 carbon atoms, or 6 to 10 carbon atoms or 12 to 22 carbon atoms Optionally, the anion is selected from methylsulfate and salicylate.

Optionally, the ionic liquid is selected from the group consisting of choline salicylate, tris-(2-hydroxyethyl) methylammonium methylsulfate and mixtures thereof.

Optionally, the ionic liquid is choline salicylate.

Optionally, the ionic liquid is tris-(2-hydroxyethyl) methylammonium methylsulfate.

Optionally, the ionic liquid is present in the composition in an amount of about 0.1 wt % to about 30 wt % based on the total weight of the composition.

Optionally, the ionic liquid is present in the composition in an amount of about 0.5 wt % to about 20 wt % based on the total weight of the composition.

Optionally, the ionic liquid is present in the composition in an amount of about 5 wt % to about 15 wt % based on the total weight of the composition.

Optionally, the ionic liquid is present in the composition in an amount of about 8 wt % to about 10 wt % based on the total weight of the composition.

Optionally, the ionic liquid is present in the composition at a concentration of about 1 mM to about 500 mM.

Optionally, the ionic liquid is present in the composition at a concentration of about 5 mM to about 300 mM.

Optionally, the ionic liquid is present in the composition at a concentration of about 15 mM to about 250 mM or about 1 mM to about 50 mM.

Optionally, the composition comprises an abrasive in an amount of less than 0.1 wt % based on the total weight of the composition.

Optionally, the composition comprises an abrasive in an amount of less than 0.01 wt % based on the total weight of the composition.

Optionally, the composition is substantially free of any abrasives.

Optionally, the composition further comprises one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, abrasives and mixtures thereof.

Optionally, the composition comprises a surfactant selected from polysorbate 20, polysorbate 80, PEG 40, or a PEG-PPG-PEG block copolymer.

Optionally, the surfactant is present in the oral care composition in an amount of about 0.75 wt % to 1.5 wt % based on the total weight of the composition.

Optionally, the composition comprises a humectant selected from glycerin, sorbitol, propylene glycol and mixtures thereof.

Optionally, glycerin is present in an amount of about 0.1 wt % to about 15 wt %, sorbitol is present in an amount of about 0.1 wt % to about 20 wt % based on the total weight of the composition, and propylene glycol is present in an amount of about 0.1 wt % to about 7 wt % based on the total weight of the composition, based on the total weight of the composition.

Optionally, glycerin is present in an amount of about 15 wt % to about 40 wt %, sorbitol is present in an amount of about 20 wt % to about 40 wt % based on the total weight of the composition, and propylene glycol is present in an amount of about 10 wt % to about 40 wt % based on the total weight of the composition, based on the total weight of the composition.

Optionally, the antibacterial agent is cetyl pyridinium chloride (CPC).

Optionally, the composition disrupts, detaches or removes plaque from the oral cavity.

Optionally, the method comprises treating or preventing a disease or condition of the oral cavity.

Optionally, the disease or condition of the oral cavity is one or more of dental caries, tartar/calculus, erosion, gingivitis, periodontal disease, halitosis or xerostomia (dry mouth).

In a third aspect, the present invention provides a method of dissolving early morning salivary sediment in the oral cavity of a subject, comprising administering a therapeutically effective amount of an oral care composition comprising at least one ionic liquid to the subject, wherein the ionic liquid comprises:

a) a quaternary ammonium cation of the formula

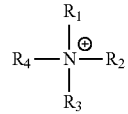

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

Optionally, $R_1$, $R_2$, $R_3$ and $R_4$ are independently selected from substituted or unsubstituted alkyl and alkenyl moieties.

Optionally, at least one of $R_1$, $R_2$, $R_3$ and $R_4$ is a hydroxyalkyl group.

Optionally, one of $R_1$, $R_2$, $R_3$ and $R_4$ is a hydroxyalkyl group and three of $R_1$, $R_2$, $R_3$ and $R_4$ are substituted or unsubstituted alkyl groups.

Optionally, two of $R_1$, $R_2$, $R_3$ and $R_4$ are hydroxyalkyl groups and two of $R_1$, $R_2$, $R_3$ and $R_4$ are substituted or unsubstituted alkyl groups.

Optionally, three of $R_1$, $R_2$, $R_3$ and $R_4$ are hydroxyalkyl groups and one of $R_1$, $R_2$, $R_3$ and $R_4$ is a substituted or unsubstituted alkyl group.

Optionally, the hydroxyalkyl group is a $C_1$-$C_6$ hydroxyalkyl group.

Optionally, the hydroxyalkyl group is a $C_1$-$C_4$ hydroxyalkyl group.

Optionally, the hydroxyalkyl group is a hydroxyethyl group.

Optionally, the hydroxyalkyl group is a hydroxymethyl group.

Optionally, the alkyl group is a substituted or unsubstituted $C_1$-$C_6$ alkyl group.

Optionally, the alkyl group is a substituted or unsubstituted $C_1$-$C_4$ alkyl group.

Optionally, the alkyl group is an ethyl group.

Optionally, the alkyl group is a methyl group.

Optionally, the alkenyl group is a $C_2$-$C_6$ alkenyl group.

Optionally, the quaternary ammonium cation is choline or tris-(2-hydroxyethyl) methylammonium.

Optionally, the halide ion is a chloride ion or a bromide ion.

Optionally, the alkylsulfate or alkyl phosphate comprises from 1 to 22 carbon atoms; optionally 1 to 4 carbon atoms, or 6 to 10 carbon atoms or 12 to 22 carbon atoms Optionally, the anion is selected from methylsulfate and salicylate.

Optionally, the ionic liquid is selected from the group consisting of choline salicylate, tris-(2-hydroxyethyl) methylammonium methylsulfate and mixtures thereof.

Optionally, the ionic liquid is choline salicylate.

Optionally, the ionic liquid is tris-(2-hydroxyethyl) methylammonium methylsulfate.

Optionally, the ionic liquid is present in the composition in an amount of about 0.1 wt % to about 30 wt % based on the total weight of the composition.

Optionally, the ionic liquid is present in the composition in an amount of about 0.5 wt % to about 20 wt % based on the total weight of the composition.

Optionally, the ionic liquid is present in the composition in an amount of about 5 wt % to about 15 wt % based on the total weight of the composition.

Optionally, the ionic liquid is present in the composition in an amount of about 8 wt % to about 10 wt % based on the total weight of the composition.

Optionally, the ionic liquid is present in the composition at a concentration of about 10 mM to about 500 mM.

Optionally, the ionic liquid is present in the composition at a concentration of about 50 mM to about 300 mM.

Optionally, the ionic liquid is present in the composition at a concentration of about 150 mM to about 250 mM.

Optionally, the composition comprises an abrasive in an amount of less than 0.1 wt % based on the total weight of the composition.

Optionally, the composition comprises an abrasive in an amount of less than 0.01 wt % based on the total weight of the composition.

Optionally, the composition is substantially free of any abrasives.

Optionally, the composition further comprises one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, abrasives and mixtures thereof.

Optionally, the composition comprises a surfactant selected from polysorbate 20, polysorbate 80, PEG 40, or a PEG-PPG-PEG block copolymer.

Optionally, the surfactant is present in the oral care composition in an amount of about 0.75 wt % to 1.5 wt % based on the total weight of the composition.

Optionally, the composition comprises a humectant selected from glycerin, sorbitol, propylene glycol and mixtures thereof.

Optionally, glycerin is present in an amount of about 0.1 wt % to about 15 wt %, sorbitol is present in an amount of about 0.1 wt % to about 20 wt % based on the total weight of the composition, and propylene glycol is present in an amount of about 0.1 wt % to about 7 wt % based on the total weight of the composition, based on the total weight of the composition.

Optionally, glycerin is present in an amount of about 15 wt % to about 40 wt %, sorbitol is present in an amount of about 20 wt % to about 40 wt % based on the total weight of the composition, and propylene glycol is present in an amount of about 10 wt % to about 40 wt % based on the total weight of the composition, based on the total weight of the composition.

Optionally, the antibacterial agent is cetyl pyridinium chloride (CPC).

Optionally, the method comprises treating or preventing a disease or condition of the oral cavity.

Optionally, the disease or condition of the oral cavity is one or more of dental caries, tartar/calculus, erosion, gingivitis, periodontal disease, halitosis or xerostomia (dry mouth)

In a fourth aspect, the present invention provides a method of disrupting and dissolving biofilm on an oral surface, comprising administering an effective amount of a composition comprising at least one ionic liquid to the surface, wherein the ionic liquid comprises:

a) a quaternary ammonium cation of the formula

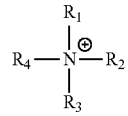

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

Optionally, $R_1$, $R_2$, $R_3$ and $R_4$ are independently selected from substituted or unsubstituted alkyl and alkenyl moieties.

Optionally, at least one of $R_1$, $R_2$, $R_3$ and $R_4$ is a hydroxyalkyl group.

Optionally, one of $R_1$, $R_2$, $R_3$ and $R_4$ is a hydroxyalkyl group and three of $R_1$, $R_2$, $R_3$ and $R_4$ are substituted or unsubstituted alkyl groups.

Optionally, two of $R_1$, $R_2$, $R_3$ and $R_4$ are hydroxyalkyl groups and two of $R_1$, $R_2$, $R_3$ and $R_4$ are substituted or unsubstituted alkyl groups.

Optionally, three of $R_1$, $R_2$, $R_3$ and $R_4$ are hydroxyalkyl groups and one of $R_1$, $R_2$, $R_3$ and $R_4$ is a substituted or unsubstituted alkyl group.

Optionally, the hydroxyalkyl group is a $C_1$-$C_6$ hydroxyalkyl group.

Optionally, the hydroxyalkyl group is a $C_1$-$C_4$ hydroxyalkyl group.

Optionally, the hydroxyalkyl group is a hydroxyethyl group.

Optionally, the hydroxyalkyl group is a hydroxymethyl group.

Optionally, the alkyl group is a substituted or unsubstituted $C_1$-$C_6$ alkyl group.

Optionally, the alkyl group is a substituted or unsubstituted $C_1$-$C_4$ alkyl group.

Optionally, the alkyl group is an ethyl group.

Optionally, the alkyl group is a methyl group.

Optionally, the alkenyl group is a $C_2$-$C_6$ alkenyl group.

Optionally, the quaternary ammonium cation is choline or tris-(2-hydroxyethyl) methylammonium.

Optionally, the halide ion is a chloride ion or a bromide ion.

Optionally, the alkylsulfate or alkyl phosphate comprises from 1 to 22 carbon atoms; optionally 1 to 4 carbon atoms, or 6 to 10 carbon atoms or 12 to 22 carbon atoms Optionally, the anion is selected from methylsulfate and salicylate.

Optionally, the ionic liquid is selected from the group consisting of choline salicylate, tris-(2-hydroxyethyl) methylammonium methylsulfate and mixtures thereof.

Optionally, the ionic liquid is choline salicylate.

Optionally, the ionic liquid is tris-(2-hydroxyethyl) methylammonium methylsulfate.

Optionally, the ionic liquid is present in the composition in an amount of about 0.1 wt % to about 30 wt % based on the total weight of the composition.

Optionally, the ionic liquid is present in the composition in an amount of about 0.5 wt % to about 20 wt % based on the total weight of the composition.

Optionally, the ionic liquid is present in the composition in an amount of about 5 wt % to about 15 wt % based on the total weight of the composition.

Optionally, the ionic liquid is present in the composition in an amount of about 8 wt % to about 10 wt % based on the total weight of the composition.

Optionally, the ionic liquid is present in the composition at a concentration of about 10 mM to about 500 mM.

Optionally, the ionic liquid is present in the composition at a concentration of about 50 mM to about 300 mM.

Optionally, the ionic liquid is present in the composition at a concentration of about 150 mM to about 250 mM.

Optionally, the composition comprises an abrasive in an amount of less than 0.1 wt % based on the total weight of the composition.

Optionally, the composition comprises an abrasive in an amount of less than 0.01 wt % based on the total weight of the composition.

Optionally, the composition is substantially free of any abrasives.

Optionally, the composition further comprises one or more agents selected from diluents, bicarbonate salts, pH modifying agents, surfactants, foam modulators, thickening agents, viscosity modifiers, humectants, sweeteners, flavorants, pigments, antibacterial agents, anticaries agents, anticalculus or tartar control agents, abrasives and mixtures thereof.

Optionally, the composition comprises a surfactant selected from polysorbate 20, polysorbate 80, PEG 40, or a PEG-PPG-PEG block copolymer.

Optionally, the surfactant is present in the oral care composition in an amount of about 0.75 wt % to 1.5 wt % based on the total weight of the composition.

Optionally, the composition comprises a humectant selected from glycerin, sorbitol, propylene glycol and mixtures thereof.

Optionally, glycerin is present in an amount of about 0.1 wt % to about 15 wt %, sorbitol is present in an amount of about 0.1 wt % to about 20 wt % based on the total weight of the composition, and propylene glycol is present in an amount of about 0.1 wt % to about 7 wt % based on the total weight of the composition, based on the total weight of the composition.

Optionally, glycerin is present in an amount of about 15 wt % to about 40 wt %, sorbitol is present in an amount of about 20 wt % to about 40 wt % based on the total weight of the composition, and propylene glycol is present in an amount of about 10 wt % to about 40 wt % based on the total weight of the composition, based on the total weight of the composition.

Optionally, the antibacterial agent is cetyl pyridinium chloride (CPC).

Optionally, the composition disrupts, detaches or removes plaque from the oral cavity.

Optionally, the method comprises treating or preventing a disease or condition of the oral cavity.

Optionally, the disease or condition of the oral cavity is one or more of dental caries, tartar/calculus, erosion, gingivitis, periodontal disease, halitosis or xerostomia (dry mouth)

In a fifth aspect, the present invention provides use of an ionic liquid for removing or reducing plaque from the oral cavity of a subject, wherein the ionic liquid comprises:

a) a quaternary ammonium cation of the formula

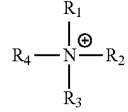

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

In a sixth aspect, the present invention provides use of an ionic liquid for dissolving early morning salivary sediment, wherein the ionic liquid comprises:

a) a quaternary ammonium cation of the formula

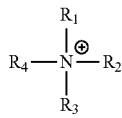

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate In a seventh aspect, the present invention provides use of an ionic liquid for disrupting and dissolving biofilm on an oral surface, wherein the ionic liquid comprises:

a) a quaternary ammonium cation of the formula

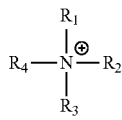

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

In an eighth aspect, the present invention provides use of the ionic liquid choline salicylate for simultaneously a) removing or reducing plaque in the oral cavity of a subject, and b) reducing the amount of bacteria in the oral cavity of a subject.

DESCRIPTION OF THE INVENTION

It should be understood that the detailed description and specific examples, while indicating embodiments of the invention, are intended for purposes of illustration only and are not intended to limit the scope of the invention.

As used throughout, ranges are used as shorthand for describing each and every value that is within the range. Any value within the range can be selected as the terminus of the range.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "about", when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition unless otherwise indicated.

In some embodiments, the present invention provides an oral care composition comprising an ionic liquid, wherein the ionic liquid comprises:

a) a quaternary ammonium cation of the formula

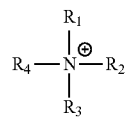

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate;

wherein the oral care composition is a mouth rinse, toothpaste, toothpowder, oral bead or strip, fluid-encased dental strip, irrigation fluid, plaque removal liquid, dental floss, hard candy, soft candy, lozenge, chewing gum, patches (e.g. intra oral patch similar to smokeless tobacco pouches) or lollipop. When used in animals or pets, veterinary pastes, chewables or treats may also be used as the delivery form.

Quaternary Ammonium Cation

A quaternary ammonium cation as used in the context of the present invention has the structure as shown in Formula 1, below, wherein $R_1$, $R_2$, $R_3$ and $R_4$ are each an organic moiety and may be the same or different, and at least one of $R_1$, $R_2$, $R_3$ and $R_4$ includes a hydroxyl group:

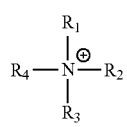

Formula 1

In some embodiments, $R_1$, $R_2$, $R_3$ and $R_4$ are independently selected from substituted or unsubstituted alkyl and alkenyl moieties. As used herein, the term "alkyl" refers to a saturated aliphatic hydrocarbon, including straight-chain, branched-chain and cycloalkyl groups of 1 to 20 carbon atoms. Alkyl groups include methyl, ethyl, propyl, butyl, pentyl, hexyl, heptyl, octyl, nonyl and decyl.

In some embodiments, at least one of $R_1$, $R_2$, $R_3$ and $R_4$ is a hydroxyalkyl group. In some embodiments, the hydroxyalkyl group is a $C_1$-$C_6$ hydroxyalkyl group, or a $C_1$-$C_4$ hydroxyalkyl group.

In some embodiments, the hydroxyalkyl group is a hydroxyethyl group. In some embodiments, the hydroxyalkyl group is a hydroxymethyl group.

In some embodiments, one of $R_1$, $R_2$, $R_3$ and $R_4$ is a hydroxyalkyl group and three of $R_1$, $R_2$, $R_3$ and $R_4$ are substituted or unsubstituted alkyl groups. In other embodiments, two of $R_1$, $R_2$, $R_3$ and $R_4$ are hydroxyalkyl groups and two of $R_1$, $R_2$, $R_3$ and $R_4$ are substituted or unsubstituted alkyl groups. In other embodiments, three of $R_1$, $R_2$, $R_3$ and $R_4$ are hydroxyalkyl groups and one of $R_1$, $R_2$, $R_3$ and $R_4$ is a substituted or unsubstituted alkyl group.

In some embodiments, the alkyl group is a substituted or unsubstituted $C_1$-$C_6$ alkyl group, or a substituted or unsubstituted $C_1$-$C_4$ alkyl group. In some embodiments, the alkyl group is an ethyl group. In some embodiments, the alkyl group is a methyl group In some embodiments, the quaternary ammonium cation is choline or tris-(2-hydroxyethyl) methylammonium.

Anions

Anions which may be used in the present invention are salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

As used herein, the term "halide" refers to F, Cl, Br, I. In some embodiments, the anion is a halide selected from Cl and Br.

As used herein, the term "alkyl" is as defined above.

In some embodiments, the alkylsulfate or alkyl phosphate comprises from 1 to 22 carbon atoms. Optionally, the alkyl sulfate and alkyl phosphate comprise 1 to 4 carbon atoms, or 6 to 10 carbon atoms or 12 to 22 carbon atoms In some embodiments, the anion is selected from methylsulfate and salicylate.

Ionic Liquid

An ionic liquid is a class of salt comprising a cation and an anion that is in liquid at a temperature of 100° C. or less and commonly have melting points below room temperature.

Any anion mentioned above may be used in combination with any of the quaternary ammonium cations defined above to form the oral care composition of the present invention.

In some embodiments, the ionic liquid is selected from choline salicylate, tris (2-hydroxyethyl) methylammonium methylsulfate (Tris-HMAM), and mixtures thereof.

In some embodiments, the ionic liquid is choline salicylate. In some embodiments, the ionic liquid is tris (2-hydroxyethyl) methylammonium methylsulfate (Tris-HMAM). The structures of choline salicylate and tris-(2-hydroxyethyl) methylammonium methylsulfate are shown below:

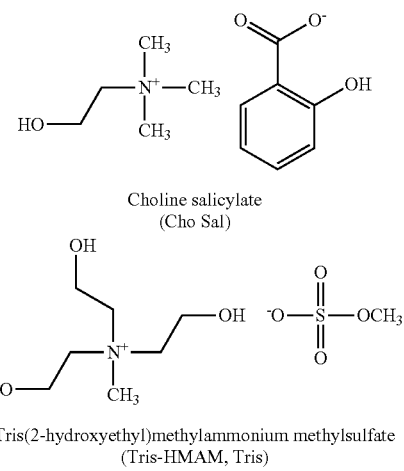

Choline salicylate
(Cho Sal)

Tris(2-hydroxyethyl)methylammonium methylsulfate
(Tris-HMAM, Tris)

In some embodiments, the ionic liquid is present in the oral care composition in an amount of about 0.1 wt % to about 30 wt % based on the total weight of the composition; optionally about 0.5 wt % to about 20 wt % based on the total weight of the composition; further optionally about 5 wt % to about 15 wt % based on the total weight of the composition; further optionally about 7 wt % to about 12 wt % based on the total weight of the composition; still further optionally about 8 wt % to about 10 wt % based on the total weight of the composition.

In some embodiments, the ionic liquid is present in the oral care composition at a concentration of about 1 mM to about 500 mM; optionally about 4 mM to about 400 mM; optionally about 5 mM to about 300 mM; optionally about 10 mM to about 270 mM; optionally about 15 mM to about 250 mM; optionally about 18 mM to about 200 mM; and optionally 1 mM to about 50 mM.

The present inventors have found that compositions containing the ionic liquids of the present invention (which have unique solvating properties) provide superior disruption, detachment, dissolution and removal of dental biofilm and plaque. Without being bound by any theory, the quaternary ammonium cations of the present invention can engage in non-covalent bonding (hydrogen bonding, ionic interactions, Van der Waals interactions etc.) and it is believed that the compositions of the present invention work by breaking the intramolecular hydrogen bonds, ionic interactions, and other non-covalent forces that hold the biofilm matrix together and the "glue" that helps the biofilm to attach to the tooth and gum tissues. By providing compositions of the present invention comprising the ionic liquids, it is believed that energetically and entropically more favourable non-covalent interactions are provided and the biofilm is therefore weakened, loosened and the physical mass and the structure of the biofilm begins to collapse and break up. Simple agitation or (for example) swishing with a mouthrinse formulation can then facilitate removal of the biofilm from oral surfaces.

In some embodiments, the oral care composition of the invention does not contain any other antibacterial or whitening agent.

Abrasives

Whilst the compositions of the present invention may optionally further comprise an abrasive which may be useful, for example, as a polishing agent, it has been found that oral care compositions comprising ionic liquids as defined herein, are effective in removing biofilm or plaque without the need for substantial amounts of abrasives. This is advantageous because abrasives can damage enamel and expose dentine tissues with repeated use, particularly, in subjects with soft enamel caused by disease or excessive exposure to food acids.

In one embodiment, the oral care composition comprises an abrasive in an amount of less than 0.1 wt % based on the total weight of the composition.

In one embodiment, the oral care composition comprises an abrasive in an amount of less than 0.01 wt % based on the total weight of the composition.

In yet another embodiment, the composition is substantially free, or free, of any abrasives.

Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

Carriers

Among useful carriers for optional inclusion in a composition of the invention are diluents, bicarbonate salts, pH modifying agents, surfactants, foam modulators, thickening agents, viscosity modifiers, humectants, sweeteners, flavorants, pigments, antibacterial agents, anticaries agents, and anticalculus or tartar control agents and abrasives. Carriers should be selected for compatibility with each other and with other ingredients of the composition.

Water is a preferred diluent and in some compositions such as mouthwashes, water is commonly accompanied by an alcohol, e.g., ethanol. The weight ratio of water to alcohol in a mouthwash composition is generally 1:1 to 20:1, for example 3:1 to 20:1 or 4:1 to 10:1.

In a further embodiment, the composition of the invention comprises at least one bicarbonate salt, useful for example to impart a "clean feel" to teeth and gums due to effervescence and release of carbon dioxide. Any orally acceptable bicarbonate can be used, including without limitation, alkali metal bicarbonates such as sodium and potassium bicarbonates, ammonium bicarbonate and the like. One or more bicarbonate salts are optionally present in a total amount of about 0.1 wt % to about 50 wt %, for example about 1 wt % to 20 wt %, by total weight of the composition.

In a still further embodiment, the composition of the invention comprises at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

In a still further embodiment, the composition of the invention comprises at least one surfactant. Any orally acceptable surfactant, most of which are anionic, nonionic or amphoteric, can be used. Suitable anionic surfactants include without limitation, water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation, poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation, derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of about 0.01 wt % to about 10 wt %, for example, from about 0.05 wt % to about 5 wt %, or from about 0.1 wt % to about 2 wt % by total weight of the composition.

In certain embodiments of the invention, the composition comprises a surfactant selected from polysorbate 20 (such as Tween® 20 as sold by Croda International), polysorbate 80 (such as Tween® 80 as sold by Croda International), PEG 40, or a [polyethylene glycol]-[polypropylene glycol]-[polyethylene glycol] (PEG-PPG-PEG) block copolymer such as Pluronic® F108 and Pluronic® F127 (as sold by BASF Corporation). In these embodiments, the surfactant may be present in the composition in an amount of 0.75 wt % to 1.5 wt % based on the total weight of the composition.

In a still further embodiment, the composition of the invention comprises at least one foam modulator, useful for example to increase amount, thickness or stability of foam generated by the composition upon agitation. Any orally acceptable foam modulator can be used, including without limitation, polyethylene glycols (PEGs), also known as polyoxyethylenes. High molecular weight PEGs are suitable, including those having an average molecular weight of 200,000 to 7,000,000, for example 500,000 to 5,000,000, or 1,000,000 to 2,500,000. One or more PEGs are optionally present in a total amount of about 0.1 wt % to about 10 wt %, for example from about 0.2 wt % to about 5 wt %, or from about 0.25 wt % to about 2 wt %, by total weight of the composition.

In a still further embodiment, the composition of the invention comprises at least one thickening agent, useful for example to impart a desired consistency and/or mouth feel to the composition. Any orally acceptable thickening agent can be used, including without limitation, carbomers, also known as carboxyvinyl polymers, carrageenans, also known as Irish moss and more particularly t-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof. One or more thickening agents are optionally present in a total amount of from about 0.01 wt % to 15 wt %, for example from about 0.1 wt % to about 10 wt %, or from about 0.2 wt % to about 5 wt %, by total weight of the composition.

In a still further embodiment, the composition of the invention comprises at least one viscosity modifier, useful for example to inhibit settling or separation of ingredients or to promote re-dispersibility upon agitation of a liquid composition. Any orally acceptable viscosity modifier can be used, including without limitation, mineral oil, petrolatum, clays and organomodified clays, silica and the like. One or more viscosity modifiers are optionally present in a total amount of from about 0.01 wt % to about 10 wt %, for example, from about 0.1 wt % to about 5 wt %, by total weight of the composition.

In a still further embodiment, the composition of the invention comprises at least one humectant. Any orally acceptable humectant can be used, including without limitation, polyhydric alcohols such as glycerin, sorbitol, xylitol or low molecular weight PEGs. Most humectants also function as sweeteners. One or more humectants are optionally present in a total amount of from about 1 wt % to about 70 wt %, for example, from about 1 wt % to about 50 wt %, from about 2 wt % to about 25 wt %, or from about 5 wt % to about 15 wt %, by total weight of the composition.

In certain embodiments, the composition of the invention comprises a humectant selected from glycerin, sorbitol, propylene glycol and mixtures thereof. In one embodiment, glycerin is present in an amount of about 0.1 wt % to about 15 wt % based on the total weight of the composition, sorbitol is present in an amount of about 0.1 wt % to about 20 wt % based on the total weight of the composition, and propylene glycol is present in an amount of about 0.1 wt % to about 7 wt % based on the total weight of the composition. In another embodiment, glycerin is present in an amount of about 15 wt % to about 40 wt % based on the total weight of the composition, sorbitol is present in an amount of about 20 wt % to about 40 wt % based on the total weight of the composition, and propylene glycol is present in an amount of about 10 wt % to about 40 wt % based on the total weight of the composition.

The present inventors have surprisingly found that an increase in the concentration of the humectants in the composition increases the level of biofilm removal by the composition.

In a still further embodiment, a composition of the invention comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.005 wt % to 5 wt %, by total weight of the composition, optionally 0.05 wt % by total weight of the composition.

In a still further embodiment, a composition of the invention comprises at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, *eucalyptus* oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, *eucalyptus* oil, eucalyptol, anethole, eugenol, *cassia*, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of from about 0.01 wt % to about 5 wt %, for example, from about 0.1 wt % to about 2.5 wt %, by total weight of the composition.

In a further embodiment, a composition of the invention may comprise an antibacterial agent. Optionally, the antibacterial agent is cetyl pyridinium chloride (CPC).

In a still further embodiment, a composition of the invention may comprise at least one colorant. Colorants herein include pigments, dyes, lakes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of from about 0.001 wt % to about 20 wt %, for example, from about 0.01 wt % to about 10 wt %, or from about 0.1 wt % to about 5 wt %, by total weight of the composition.

In some embodiments, the composition comprises a fluoride ion sources. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply about 50 to about 5000 ppm fluoride ion, e.g., from about 100 to about 1000, from about 200 to about 500, or about 250 ppm fluoride ion. Fluoride ion sources may be added to the compositions of the invention at a level of about 0.001 wt % to about 10 wt %, e.g., from about 0.003 wt % to about 5 wt %, 0.01 wt % to about 1 wt, or about 0.05 wt %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

The composition of the present invention optionally comprises a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The composition of the present invention optionally incorporates one or more antisensitivity agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1 wt % to about 20 wt % by weight based on the total weight of the composition, depending on the agent chosen. The compositions of the present invention may also be used to treat hypersensitivity by blocking dentin tubules when applied to a tooth.

In some embodiments, the composition of the invention further comprises an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

In another embodiment, the composition comprises an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of from about 0.05 wt % to about 3 wt %, for example from about 0.1 wt % to about 1 wt %, by total weight of the composition.

The composition of the present invention may additionally optionally comprise a tartar control (anticalculus) agent as provided below. Tartar control agents among those useful herein include salts of the specified agents, including alkali metal and ammonium salts. The agents include: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof. Other useful tartar control agents include polycarboxylate polymers and polyvinyl methyl ether/maleic anhydride (PVM/MA) copolymers, such as GANTREZ®.

In some embodiments, the composition of the present invention further comprises a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophan, L-lysine, methionine, threonine, levocarnitine and L-carnitine), lipotropics (such as choline, inositol, betaine, and linoleic acid), and mixtures thereof.

Delivery

The oral care composition of the present invention is a mouth rinse, toothpaste, toothpowder, oral bead or strip, fluid-encased dental strip, irrigation fluid, plaque removal liquid, dental floss, hard candy, soft candy, lozenge, chewing gum, or lollipop.

The oral care composition of the present invention preferably comprises an orally acceptable carrier for use in a product such as a mouth rinse (including dual phase mouthwash), toothpaste, actives in beads/strips, irrigation fluids, plaque removal fluids, bead formulas, formulations to be delivered through devices such as pens, back of a toothbrush and front of a toothbrush, formulations to be delivered through porous wicking materials, interdental brushes, fluid encased dental strips, floss impregnated or coated with the formulations or dried formulations, portables, oral trays, hard or soft candy, lozenge with a soft plaque dissolving liquid inside, lollipops with the plaque dissolving formulation imbedded into the lickable "candy" that can also help control tongue bacteria, peelable gels, patches, formulations for pop-rocks that, upon popping, spread a fine mist of the formulation around the oral cavity, tongue cleaners with plaque dissolving strips and dental strips. Accordingly, opportunities exist for professional use of the compositions of the present invention (e.g. during cleanings, irrigations, or aggressive periodontal procedures, such as root planning & scaling). In some embodiments, the composition of the invention may be provided in any of the products defined herein.

A typical formulation for incorporation into a Wisp® bead formulation is shown in Table 1 below:

TABLE 1

| Ingredient Name | Wt % Plaque dissolving WISP formula |
|---|---|
| Castor Oil | 43.5 |
| Flavor | 15 |
| WS-3-Cooling sensate | 1.5 |
| 10% Sucralose solution | 5 |
| Ionic Liquid | 0.3-5 |
| Propylene glycol | Balance |

A typical formulation for use with a wick delivery device or in an interdental wicking brush is shown in Table 2 below:

TABLE 2

| Ingredient Name | Wt % Plaque dissolving formula |
|---|---|
| Glycerin | 15 |
| Propylene glycol | 30 |
| Flavor (89-186) | 8 |
| WS3-Cooling sensate | 3 |
| 10% Sucralose solution | 5 |
| Ionic Liquid | 0.3-10 |
| Water pH adjusted if necessary | Balance |

In one embodiment, the oral care composition of the invention can be dried into powder and utilized in a portable sachet. For example, upon mixing such a powder with a suitable solvent such as water, a rinse may be created to remove plaque, proteins and other debris in the mouth.

In another embodiment, the composition of the invention can be dried with abrasives such as silica, calcium carbonate or soft capsules that upon addition of small amount of water, creates a paste to brush away the plaque.

Formulations that increase the substantivity of ionic liquids onto a surface could be expected to increase the efficacy of biofilm, and hence plaque removal. For example, Tween® 20 while also functioning as a surfactant, is also a wetting agent. Therefore, incorporation of such an agent could be expected to increase the wettability and spreading of a mouth rinse formulation according to the present invention, over the soft and hard tissue, increasing the formulation's propensity for plaque dissolution and removal.

Methods of Use

The composition according to the present invention may be administered to or applied to a human or other animal subject. The composition may be suitable for administration or application to the oral cavity of a human or animal subject. Typically, the composition is for reducing or removing dental plaque. The reduction or removal of plaque may occur through an inhibition of biofilm (a plaque precursor) formation and/or degradation of microbial biofilm.

In some embodiments, the oral care composition of the present invention is for removing or reducing plaque.

In some embodiments, the oral care composition of the present invention is for dissolving early morning salivary sediment.

In some embodiments, the oral care composition of the present invention is for disrupting and dissolving biofilm.

In some embodiments, the oral care composition of the present invention is for treating or preventing a disease or condition of the oral cavity. Typically, the disease or condition is caused by plaque or biofilm. In some embodiments, the disease or condition of the oral cavity is one or more of dental caries, tartar/calculus, erosion, gingivitis, periodontal disease, halitosis or xerostomia (dry mouth) Accordingly, the present invention also provides a composition as defined above for use as a medicament.

The present invention also provides a method of removing or reducing plaque from the oral cavity of a subject, comprising administering a therapeutically effective amount of a composition comprising at least one ionic liquid to the subject, wherein the ionic liquid comprises:

a) a quaternary ammonium cation of the formula

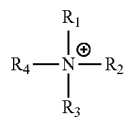

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

In some embodiments, the composition disrupts, detaches or removes plaque from the oral cavity. In some embodiments, the method comprises treating or preventing a disease or condition of the oral cavity. In certain embodiments, the disease or condition of the oral cavity is one or more of dental caries, tartar/calculus, erosion, gingivitis, periodontal disease, halitosis or xerostomia (dry mouth).

The present invention also provides a method of dissolving early morning salivary sediment in the oral cavity of a subject, comprising administering a therapeutically effective amount of an oral care composition comprising at least one ionic liquid to the subject, wherein the ionic liquid comprises:

a) a quaternary ammonium cation of the formula

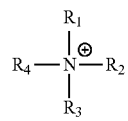

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

In some embodiments, the method comprises treating or preventing a disease or condition of the oral cavity. In certain embodiments, the disease or condition of the oral cavity is one or more of dental caries, tartar/calculus, erosion, gingivitis, periodontal disease, halitosis or xerostomia (dry mouth)

The present invention further provides a method of disrupting and dissolving biofilm on an oral surface, comprising administering an effective amount of a composition comprising at least one ionic liquid to the surface, wherein the ionic liquid comprises:

a) a quaternary ammonium cation of the formula

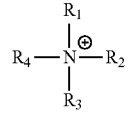

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

In some embodiments, the composition disrupts, detaches or removes plaque from the oral cavity. In some embodiments, the method comprises treating or preventing a disease or condition of the oral cavity. In certain embodiments, the disease or condition of the oral cavity is one or more of dental caries, tartar/calculus, erosion, gingivitis, periodontal disease, halitosis or xerostomia (dry mouth).

The present invention further provides a use of an ionic liquid for removing or reducing plaque from the oral cavity of a subject, wherein the ionic liquid comprises:

a) a quaternary ammonium cation of the formula

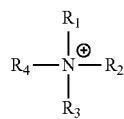

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

The present invention further provides a use of an ionic liquid for dissolving early morning salivary sediment, wherein the ionic liquid comprises:

a) a quaternary ammonium cation of the formula

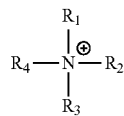

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

The present invention also provides a use of an ionic liquid for disrupting and dissolving biofilm on an oral surface, wherein the ionic liquid comprises:

a) a quaternary ammonium cation of the formula

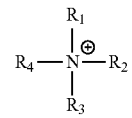

wherein $R_1$, $R_2$, $R_3$ and $R_4$ are each an organic moiety and may be the same or different, and at least one of $R_1$, $R_2$, $R_3$ and $R_4$ includes a hydroxyl group; and b) an anion selected from the group consisting of salicylate, acetate, halide, phosphate, alkyl phosphate, phosphonate, pyrophosphate, hexametaphosphate, polymetaphosphate, orthophosphate, tripolyphosphate, sulfate, alkyl sulfate (e.g. methylsulfate, ethylsulfate), lauryl sulfate, phenolsulfate. benzoate, acetylacetonate, carboxylate, citrate, ascorbate, dicyamide, L- or D-amino acids (e.g. arginate, glycinate, prolinate, etc.), glycolate, gluconate, maleate, sweetener anions (e.g. saccharinate, aspartamate, cyclamate), hydroxide, succinate, tartrate, docusate, linoleate, oleate, and tosylate.

Compositions comprising a quaternary ammonium cation as defined above and an anion as defined above are highly effective in reducing biofilm, removing or reducing plaque, and dissolving early morning salivary sediment. They possess the ability to offer a deep but gentle cleaning and promote removal of biofilm and plaque without the need for harsh abrasives or rigourous brushing.

The present invention also provides a use of the ionic liquid choline salicylate for simultaneously a) removing or reducing plaque in the oral cavity of a subject, and b) reducing the amount of bacteria in the oral cavity of a subject.

The invention is further illustrated in the following non-limiting examples.

EXAMPLES

Example 1

In Vitro Evaluation of Bio-Film Removal Efficacy

General Procedures Used to Prepare Biofilm

Saliva Preparation: Saliva was collected from the analyst who is a healthy adult with no history of antibiotic use in the previous week and does not require routine medications. The analyst used a commercially available fluoride dentifrice and a soft bristled toothbrush for routine oral hygiene for 3 days prior to the start of saliva collection. Saliva was collected in the morning, at least two hours after a meal and was centrifuged at 10,000 rpm for 20 minutes. The supernatant was decanted into a Petri dish and placed under UV for 45 minutes.

Bacteria Preparation: Bacteria were taken from the artificial mouth consortium (containing *Actinomyces naeslundii, Streptococcus oralis, Veillonella parvula, Lactobacillus casei,* and *Fusibacterium nucleatum*) and *Streptococcus mutans*, grown separately, was added to it. Bacteria were grown in trypticase soy broth media with 6% sucrose. 2 parts artificial mouth to 1 part S. mutans are mixed and diluted to the necessary volume, then diluted until an optical density of 0.2 is reached.

Optical Density Measurement: To measure the turbidity of the well, the plate is measured at 610 nm.

Plate Preparation: 500 µL of UV treated saliva were added to each well of a 24 well plate. Plates were inoculated overnight in 37° C. After inoculation, excess saliva was discarded and 1 ml of bacteria was added to each well. The bacteria were allowed to attach and develop a biofilm on the bottom of each well over 2-4 days, changing media (trypticase soy broth (TSB) media with 6% sucrose) every 48 hours. During media change, the old media was discarded and 1 ml of fresh media was added.

Treatment: 500 µL of ionic liquid formulation was added to each well and incubated for 4-30 minutes on a plate shaker at 300 rpm. After incubation, the supernatant was discarded. No rinsing is done. The optical density of each well was measured and the % reduction from the control (water) was calculated (OD of negative control−OD of sample)/(OD of negative control).

Second Treatment: 500 µL of ionic liquid formulation was added to each well and incubated for 4-30 minutes on a plate shaker at 300 rpm. After discarding the supernatant, the optical density was measured and the % reduction from the control (water) was calculated (OD of negative control−OD of sample)/(OD of negative control).

A 3-day old biofilm provided a sufficiently robust biofilm to help differentiate the efficacy of different prototype mouthwash formulations for biofilm removal. In the tests carried out on the prototype mouthrinse formulations, below:

A 3-day old biofilm was grown on a 24 well plate using the artificial mouth consortium (A. naeslundii, S. oralis, V. parvula, L. casei, F. nucleatum) of bacteria with S. mutans.
  1) Plates were inoculated with saliva overnight to form a pellicle
  2) The consortium bacteria (1 mL) at an optical density of ~0.2 was added to each well
  3) The bacterial media (TSB with 6% sucrose) was changed every 48 h The 3-day old biofilm was treated with the prototype formulation (500 µL) for 15 min on a plate shaker at 300 rpm. After incubation, the supernatant was discarded. No rinsing was performed at this time (though a second mouthrinse treatment was shown to remove more biofilm than the first treatment). The optical density of each well was measured and the percent reduction from the control (water) was calculated (OD of negative control−OD of sample)/(OD of negative control).

Prototype Mouthrinse Formulations

A statistical design-of-experiments (DOE) approach was used to develop prototype mouth rinse formulations for biofilm removal. An 8 factor design was used. A mouth rinse was used a base formulation (see Table 3). The impact of five different surfactants and their amounts (0.75-1.5%) was evaluated, in addition to the ionic liquids choline salicylate and tris (2-hydroxyethyl) methylammonium methylsulfate (Tris-HMAM), used either alone or in combination in the formulations. The influence of the anti-bacterial agent cetyl pyridinium chloride (CPC) on biofilm removal was also evaluated. The sweetener sucralose and the flavor were at kept constant concentration in all the formulations. See Table 1 for formulation design:

TABLE 3

| Ingredient | Amount (%) |
|---|---|
| Glycerin | 0-20 |
| Propylene Glycol | 0-10 |
| Sorbitol | 0-20 |
| Surfactant (Tween 80, Tween 20, PEG 40, Pluronic F108, or Pluronic F127) | 0.75-1.5 |
| Choline Salicylate and/or Tris (2-hydroxyethyl) methyl ammonium methylsulfate | 0-20 |
| Sucralose | 0.05 |
| Flavor | 0.12 |
| CPC | 0-0.075 |
| Water | balance |

74 prototype formulations were developed. There are shown Table 4 (see next page), along with the % biofilm reduction after one 15-minute treatment of a 3-day-old biofilm with the formulation, and the viscosity for each formulation. All amounts are given in wt %.
A—Formulation number
B—Glycerin
C—Polyethylene glycol
D—Sorbitol
E—CPC (cetyl pyridinium chloride)
F—Surfactant level
G—Choline salicylate
H—(tris (2-hydroxyethyl) methylammonium methylsulfate)
I—Surfactant type
J—% Biofilm reduction
K—Viscosity (cP)

TABLE 4

| A | B | C | D | E | F | G | H | I | J | K |
|---|---|---|---|---|---|---|---|---|---|---|
| 32 | 20 | 5 | 20 | 0 | 0.75 | 20 | 20 | F108 | 80 | 47 |
| 21 | 20 | 0 | 0 | 0 | 1.5 | 20 | 20 | Tween80 | 80 | 8 |
| 7 | 0 | 10 | 20 | 0 | 0.75 | 20 | 20 | Tween20 | 79 | 11 |
| 8 | 20 | 10 | 0 | 0 | 1.5 | 20 | 20 | PEG40 | 78 | 14 |
| 19 | 20 | 10 | 0 | 0.075 | 1.5 | 20 | 20 | Tween20 | 78 | 13 |
| 50 | 20 | 5 | 20 | 0.075 | 0.75 | 20 | 0 | Tween80 | 77 | 11 |
| 9 | 0 | 10 | 20 | 0.075 | 0.75 | 20 | 20 | F108 | 77 | 13 |
| 2 | 0 | 10 | 20 | 0 | 0.75 | 20 | 20 | PEG40 | 77 | 13 |
| 29 | 20 | 10 | 10 | 0 | 0.75 | 20 | 20 | Tween20 | 76 | 27 |
| 1 | 20 | 10 | 20 | 0.075 | 1.5 | 20 | 20 | Tween80 | 76 | 78 |
| 31 | 10 | 10 | 0 | 0 | 1.5 | 20 | 20 | F127 | 76 | 10 |
| 10 | 0 | 10 | 20 | 0 | 1.5 | 20 | 20 | F108 | 75 | 16 |
| 18 | 0 | 10 | 20 | 0.075 | 1.5 | 20 | 20 | F127 | 74 | 18 |
| 24 | 20 | 10 | 20 | 0.075 | 0.75 | 20 | 20 | PEG40 | 74 | 70 |
| 15 | 20 | 10 | 20 | 0 | 1.5 | 0 | 20 | F127 | 74 | 17 |
| 60 | 20 | 10 | 20 | 0.075 | 1.125 | 20 | 0 | F127 | 74 | 19 |
| 51 | 0 | 5 | 0 | 0.075 | 0.75 | 20 | 0 | F127 | 73 | 2 |
| 42 | 20 | 10 | 20 | 0.0375 | 1.5 | 0 | 20 | PEG40 | 73 | 15 |
| 13 | 20 | 0 | 20 | 0.075 | 1.5 | 20 | 20 | F127 | 73 | 35 |
| 39 | 20 | 5 | 0 | 0.075 | 0.75 | 20 | 20 | Tween80 | 73 | 10 |
| 20 | 20 | 0 | 20 | 0.075 | 1.5 | 20 | 20 | F108 | 73 | 42 |
| 40 | 20 | 0 | 20 | 0.0375 | 1.5 | 20 | 0 | Tween20 | 71 | 9 |
| 12 | 20 | 0 | 20 | 0 | 1.5 | 20 | 0 | Tween20 | 70 | 8 |
| 16 | 20 | 10 | 0 | 0.075 | 1.5 | 20 | 20 | F108 | 70 | 20 |
| 56 | 20 | 0 | 20 | 0.075 | 0.75 | 10 | 20 | Tween20 | 70 | 13 |
| 34 | 10 | 10 | 0 | 0 | 1.5 | 20 | 20 | Tween20 | 70 | 7 |
| 49 | 10 | 10 | 20 | 0 | 0.75 | 20 | 0 | Tween80 | 69 | 8 |
| 52 | 0 | 0 | 20 | 0 | 1.125 | 20 | 0 | F127 | 69 | 3 |
| 61 | 20 | 0 | 0 | 0.0375 | 0.75 | 20 | 20 | Tween20 | 69 | 7 |
| 33 | 0 | 0 | 20 | 0 | 1.5 | 10 | 20 | Tween80 | 69 | 4 |
| 22 | 0 | 0 | 10 | 0.075 | 0.75 | 20 | 20 | F127 | 68 | 4 |
| 57 | 0 | 10 | 20 | 0.075 | 0.75 | 10 | 20 | Tween80 | 68 | 7 |
| 35 | 0 | 5 | 20 | 0 | 1.5 | 20 | 0 | PEG40 | 68 | 4 |
| 62 | 20 | 10 | 0 | 0 | 0.75 | 10 | 0 | F108 | 67 | 4 |
| 27 | 0 | 0 | 10 | 0.075 | 1.5 | 20 | 20 | PEG40 | 67 | 4 |
| 30 | 20 | 0 | 20 | 0.0375 | 0.75 | 0 | 20 | Tween80 | 67 | 8 |
| 28 | 0 | 10 | 20 | 0 | 1.125 | 0 | 20 | F108 | 67 | 5 |
| 5 | 20 | 10 | 0 | 0 | 1.5 | 20 | 0 | Tween20 | 67 | 6 |
| 38 | 0 | 0 | 10 | 0.075 | 1.5 | 20 | 20 | Tween80 | 65 | 5 |

TABLE 4-continued

| A | B | C | D | E | F | G | H | I | J | K |
|---|---|---|---|---|---|---|---|---|---|---|
| 36 | 0 | 10 | 10 | 0.075 | 1.5 | 20 | 0 | Tween80 | 64 | 3 |
| 3 | 20 | 0 | 20 | 0 | 1.5 | 0 | 20 | F108 | 63 | 11 |
| 4 | 20 | 10 | 0 | 0.075 | 0.75 | 0 | 20 | F127 | 63 | 5 |
| 70 | 20 | 10 | 0 | 0.075 | 0.75 | 20 | 0 | PEG40 | 62 | 5 |
| 64 | 20 | 0 | 20 | 0 | 0.75 | 10 | 0 | PEG40 | 61 | 5 |
| 26 | 0 | 0 | 10 | 0.075 | 1.5 | 20 | 20 | F108 | 59 | 6 |
| 6 | 0 | 10 | 0 | 0 | 1.5 | 0 | 20 | Tween80 | 57 | 2 |
| 59 | 0 | 10 | 20 | 0 | 1.5 | 10 | 0 | Tween20 | 56 | 1 |
| 63 | 0 | 5 | 20 | 0.075 | 1.5 | 0 | 20 | Tween20 | 55 | 4 |
| 23 | 0 | 5 | 20 | 0 | 1.5 | 20 | 0 | F108 | 54 | 5 |
| 41 | 20 | 10 | 20 | 0 | 1.5 | 0 | 0 | Tween80 | 54 | 6 |
| 53 | 0 | 0 | 20 | 0 | 1.5 | 0 | 10 | F127 | 53 | 3 |
| 14 | 0 | 0 | 0 | 0.075 | 0.75 | 0 | 20 | PEG40 | 52 | 2 |
| 65 | 0 | 0 | 0 | 0.075 | 1.125 | 0 | 20 | F127 | 50 | 2 |
| 72 | 0 | 10 | 0 | 0 | 1.5 | 0 | 20 | Tween80 | 50 | 3 |
| 67 | 0 | 5 | 0 | 0 | 0.75 | 20 | 0 | PEG40 | 50 | 2 |
| 47 | 20 | 0 | 20 | 0.075 | 0.75 | 0 | 0 | F108 | 49 | 4 |
| 66 | 0 | 0 | 0 | 0 | 0.75 | 0 | 10 | Tween80 | 49 | 1 |
| 46 | 10 | 10 | 20 | 0.075 | 0.75 | 0 | 0 | Tween20 | 49 | 4 |
| 37 | 10 | 0 | 0 | 0.075 | 1.5 | 0 | 20 | Tween80 | 47 | 2 |
| 73 | 20 | 10 | 0 | 0 | 1.5 | 20 | 0 | Tween20 | 43 | 6 |
| 71 | 20 | 0 | 0 | 0 | 0.75 | 0 | 20 | F127 | 43 | 3 |
| 44 | 0 | 10 | 20 | 0 | 0.75 | 0 | 0 | F127 | 43 | 3 |
| 54 | 10 | 5 | 10 | 0.0375 | 1.125 | 0 | 10 | Tween20 | 42 | 3 |
| 74 | 20 | 0 | 20 | 0.075 | 1.5 | 0 | 0 | PEG40 | 41 | 4 |
| 69 | 20 | 0 | 0 | 0.075 | 1.125 | 20 | 0 | F108 | 41 | 4 |
| 17 | 20 | 0 | 20 | 0.075 | 1.5 | 0 | 0 | PEG40 | 40 | 4 |
| 43 | 0 | 0 | 0 | 0 | 1.5 | 0 | 0 | Tween20 | 31 | 1 |
| 11 | 0 | 10 | 0 | 0.075 | 1.5 | 0 | 0 | PEG40 | 31 | 2 |
| 45 | 20 | 0 | 0 | 0 | 1.125 | 0 | 0 | PEG40 | 29 | 2 |
| 55 | 0 | 10 | 0 | 0.0375 | 1.5 | 0 | 0 | F108 | 29 | 2 |
| 48 | 0 | 0 | 0 | 0 | 0.75 | 20 | 0 | F108 | 26 | 2 |
| 25 | 20 | 0 | 10 | 0.075 | 1.5 | 0 | 0 | F127 | 20 | 3 |
| 58 | 0 | 0 | 20 | 0.0375 | 0.75 | 0 | 0 | PEG40 | 15 | 2 |
| 68 | 0 | 10 | 10 | 0.075 | 0.75 | 0 | 0 | F108 | 12 | 2 |

F108 (Synperonic ® F-108 (poly(ethylene glycol)-block-poly(propylene glycol)-block-poly(ethylene glycol));
F127 (Pluronic ® F-127 (polyoxypropylenepolyoxyethylene block copolymer);
PEG40 (ethylene oxide);
Tween 20 (polyoxyethylene sorbitan monolaurate);
Tween 80 (polyoxyethylene sorbitan monooleate)

As can be seen from the results in Table 4, twenty-six (26) of the prototype formulations provided about ≥70% biofilm removal. Generally, formulations containing quaternary ammonium compounds meeting the ≥70% biofilm removal can be predicted if the formulation met the following criteria:
(i) at least one of glycerin or polyethylene glycol is present;
(ii) no more than two of glycerin (B), polyethylene glycol (C), sorbitol (D), CPC (cetyl pyridinium chloride) (E), surfactant (F), choline salicylate (G) and (tris (2-hydroxyethyl) methylammonium methylsulfate)(H) is present, unless the wt % sum of B+C+D is less than the wt % sum of F+G; and
(iii) a biofilm factor (BF) of at least 50, wherein the BF=(wt % of B+C+D+G+H)×(wt % of E+F).

The above results strongly suggest that several of the formulations identified through the design-of-experiments approach may provide clinical efficacy to disrupt, dissolve and remove plaque in vivo.

Example 2

Efficacy of Dissolution of Morning Salivary Sediment

Several of the leading prototype formulations of the present invention provide significant dissolution of early morning salivary sediment. The salivary sediment was collected without evening or early morning brushing, and the salivary supernatant was removed by decanting. Such salivary sediment contains appreciable amounts of dental plaque and left over food debris and is very difficult to dissolve and remove from the oral cavity without brushing with dentifrice.

In this example, 4 mL of the prototype formulations or mouthwash containing cetylpyridinium chloride (CPC) was added to the salivary sediment and mixed at room temperature for up to 1 minute. Commercial mouth rinses such as a mouthwash with CPC, show no early morning salivary sediment dissolution. However, it was found that formulations of the present invention helped to dissolve salivary sediment.

In general, there was a correlation between those formulations of the present invention that exhibited ≥70% biofilm removal in-vitro and salivary sediment dissolution.

Example 3

Factors and Ingredients that Impact on % Biofilm Removal

Concentration of Ionic Liquids

It was found that an increase in the amount of ionic liquid used in the formulation results in greater biofilm removal. The percent biofilm removal provided by each ionic liquid formulation is similar ca. 60%. When the two ionic liquids choline salicylate and tris (2-hydroxyethyl) methylammonium methylsulfate are used together in a formulation, the percent biofilm efficacy is increased further to >70%.

Impact of Different Ingredients in the Formulation

Testing on the impact of different ingredients on the percent biofilm removal shows that the identity of the surfactant, the percentage of surfactant used and the amount of anti-bacterial agent cetyl pyridinium chloride (0 to 0.075%) do not impact biofilm removal %.

The addition of glycerin, propylene glycol and/or sorbitol to the formulation increases the percent of biofilm removal.

Taking these results together, a few significant formulation design criteria emerge for the effective removal of a robust 3-day old in-vitro oral biofilm. These are summarized below:

Increase in choline salicylate or tris (2-hydroxyethyl) methylammonium methylsulfate provides significant increase in biofilm removal Increase in humectants increases biofilm removal: sorbitol>glycerin≈propylene glycol Surfactant and cetyl pyridinium chloride (CPC) do not impact biofilm removal: have flexibility with respect to surfactant choice and concentration (0.75-1.5%). (Flavour and sucralose at fixed concentrations).

A statistical analysis of the data reveals the percent contribution of each of the ionic liquids alone and when used together on biofilm removal (assuming that glycerin is at 10%, propylene glycol 5% and sorbitol 10%).

TABLE 5

| Choline salicylate | TRIS-based ionic liquid | Percent biofilm removal | Percent biofilm removal if sorbitol at 20% |
|---|---|---|---|
| 0 | 0 | 35 | 40 |
| 0 | 10 | 47 | 52 |
| 0 | 20 | 60 | 65 |
| 10 | 0 | 48 | 53 |
| 20 | 0 | 61 | 66 |
| 10 | 10 | 57 | 62 |
| 20 | 20 | 72 | 77 |

TABLE 5-continued

| Choline salicylate | TRIS-based ionic liquid | Percent biofilm removal | Percent biofilm removal if sorbitol at 20% |
|---|---|---|---|
| 10 | 20 | 66 | 71 |
| 20 | 10 | 60 | 65 |

TRIS = tris (2-hydroxyethyl) methylammonium methylsulfate

Since sorbitol favors biofilm removal, the impact of increasing this ingredient to 20% was calculated. 20% sorbitol in the formulations provides ~5% increase in biofilm removal (assuming that glycerin is at 10%, and propylene glycol 5%).

Table 6 (below) shows the best combination of ingredients with percent amounts for effective removal of a 3-day biofilm predicted utilizing the D-Optimal Design module in the Design-Expert® Software program (available at www.itl.nist.gov).
As discussed earlier, the surfactant type (of the five chosen) and level (0.75-1.5%) do not significantly impact on biofilm dissolution. Flavor and sucralose also do not significantly impact on biofilm dissolution when used at 0.05% and 0.12% respectively. The presence (0.075%) or absence of cetyl pyridinium chloride (CPC) does not impact biofilm dissolution.

TABLE 6

| Ingredient | Amount (%) |
|---|---|
| Glycerin | 20 |
| Propylene glycol | 10 |
| Sorbitol | 20 |
| Surfactant (Tween 80, Tween 20, PEG 40, Pluronic F108, Pluronic F127) | 1.125* |
| Choline salicylate | 20 |
| Tris (2-hydroxyethyl) methylammonium methylsulfate | 20 |
| Sucralose | 0.05 |
| Flavour | 0.12 |
| CPC | 0.075 |
| Water | balance |

*surfactant type and level (0.75-1.5).
CPC, flavour, sucralose at constant value
Predicted 3-day biofilm removal: 83.66%
Stdev: 4.56, pH = 7.26

Example 4

Enhanced Mouthrinse Compositions and their Efficacy for Biofilm Removal

From the above design-of-experiments results and the design criteria, mouthrinse formulations containing tris(2-hydroxyethyl)-methylammonium methylsulfate at different percent concentrations were developed.
Optimized Mouth Rinse Formulations Different weight percent concentrations of the ionic liquid, tris(2-hydroxyethyl) methylammonium methylsulfate (Tris-HMAM), in low and high-humectant mouth rinse formulations were assessed for their ability to remove a 3-day old multispecies oral biofilm and compared to controls: DI water, a mouthwash with 0.075% CPC and a mouthwash containing five enzymes to remove biofilm.

Low-humectant mouthrinse formulations may contain 0-15% glycerin, 0-7% propylene glycol and 0-20% sorbitol. High-humectant mouthrinse formulations may contain 15-40% glycerin, 10-40% propylene glycol and 20-40% sorbitol. See Table 7 below.

TABLE 7

| Ingredient | LOW humectant amount % | HIGH humectant amount % |
|---|---|---|
| Glycerin | 15 | 20 |
| Propylene glycol | 7 | 10 |
| Sorbitol | 10.5 | 20 |
| CPC | 0.075 | 0.075 |
| Tween 20 | 1.125 | 1.125 |
| Tris-HMAM | 0-40 | 0-40 |
| Sucralose | 0.05 | 0.05 |
| Flavour | 0.12 | 0.12 |
| water | balance | balance |

It was found that aging of the above formulations provided no stability or cosmetic issues. Other humectants can be used in place of those above.

Table 8 shows the percent removal of a 3-day old biofilm with different concentrations of tris (2-hydroxyethyl) methylammonium methylsulfate (Tris-HMAM) in low and high humectant mouth rinse formulation. As shown in Table 8, below, both low and high humectant formulations are effective in removing a 3-day-old multispecies oral biofilm:

TABLE 8

| Conc Tris-HMAM | 0% | 1% | 2.5% | 5% | 10% | 20% | 40% |
|---|---|---|---|---|---|---|---|
| % removal in Low humectant mouthwash | 12.4 | 25.6 | 28.2 | 30.9 | 46.8 | 57.3 | 67.1 |
| % removal in High humectant mouthwash | 37.3 | 39.0 | 50.5 | 53.9 | 57.7 | 71.1 | 73.2 |

Controls: deionised water and 0.07% CPC containing mouth rinse formulation remove less than 1% biofilm. A commercial mouthwash containing five enzymes in its formulation removes 31.7%.

The results shown in Table 8 illustrate that (1) the high humectant formulation removes ca. three times as much biofilm than the low humectant formulation; (2) the addition of tris (2-hydroxyethyl) methylammonium methylsulfate to either low or high humectant mouth rinse formulation enhances biofilm removal; and (3) the high humectant base mouthwash alone removes more biofilm than the commercially available five enzyme mouthwash formulation and CPC containing mouth rinses.

Varying the type, amount and the ratios of the humectants to each other can be expected to further increase the efficiency and speed of biofilm removal. Similar behaviour can be expected of other quaternary based compounds containing an alkyl hydroxyl appendage or other H-bonding or donating end group.

Example 5

Antibacterial Efficacy of Choline Salicylate

It has been shown that, when formulated at 10% concentration in a mouth rinse, choline salicylate provides greater growth inhibition of *A. viscosus* than does a mouthrinse which contains 0.075% cetyl pyridinium chloride. The results are shown in Table 9, below (Protocol: 500 microliter test sample was added to 9.5 mL *A. viscosus* in TSB (initial O.D.) at 3 replicates per sample. Bacterial optical density was captured every 0, 4, 22 and 24 hours.

TABLE 9

| Ionic Liquids-Sample ID | 0 h | 4 h | 22 h | 24 h |
|---|---|---|---|---|
| A: 1,2,4-trimethyl-pyrazolium methylsulfate | 0.1482 | 0.1978 | 0.8519 | 1.0042 |
| B: 1-ethyl-3-methylimidazolium (EMIM) bromide | 0.1482 | 0.2216 | 0.7598 | 0.8533 |
| C: Choline acetate | 0.1482 | 0.2559 | 0.9480 | 1.0385 |
| D: 1-ally1-3-methylimidazolium (AMIM) chloride | 0.1482 | 0.2265 | 0.7091 | 0.8440 |
| E: Choline salicylate | 0.1482 | 0.1523 | 0.1542 | 0.1539 |
| F: Choline chloride | 0.1482 | 0.2445 | 1.0236 | 1.0674 |
| G: Tris(2-hydroxyethyl) methylammonium methylsulfate | 0.1482 | 0.2605 | 0.8415 | 0.9087 |
| H: EMIM ethylsulfate | 0.1482 | 0.2499 | 0.7514 | 0.7965 |
| I: EMIM acetate | 0.1482 | 0.2324 | 0.7942 | 0.8223 |
| J: 1-butyl-3-methylimidazolium (BMIM) bromide | 0.1482 | 0.2373 | 0.5994 | 0.8244 |
| DI (distilled water) | 0.1482 | 0.3000 | 1.0997 | 1.2130 |
| Mouthwash with 0.075% CPC | 0.1482 | 0.1706 | 0.1540 | 0.1704 |

Growth inhibition of *A viscosus* over a 24 hour period; 500 µl test sample was added to 9.5 ml *A. viscosus* in TSB (initial O.D) at 3 replicates per sample. Bacterial optical density was captured every at 0, 4, 22 and 24 hrs.

It can be seen from the above results that the anion of the choline-containing ionic liquid appears to play a significant role in imparting this growth inhibition activity.

While particular embodiments of the invention have been illustrated and described, it will be obvious to those skilled in the art that various changes and modifications may be made without departing from the scope of the invention as defined in the appended claims.

We claim:

1. An oral care composition for removing or reducing plaque comprising an ionic liquid, wherein the ionic liquid comprises a combination of choline salicylate and tris-(2-hydroxyethyl) methylammonium methylsulfate;
   wherein the oral care composition is a mouth rinse; and
   wherein the composition comprises a humectant selected from glycerin, sorbitol, propylene glycol and mixtures thereof; and
   wherein the composition comprises a surfactant selected from polysorbate 20, polysorbate 80, polyethylene glycol 40 (PEG 40), and a [polyethylene glycol]-[polypropylene glycol]-[polyethylene glycol] (PEG-PPG-PEG) block copolymer.

2. The oral care composition of claim 1, wherein the ionic liquid is present in the oral care composition in an amount of 8 wt % to 10 wt % based on the total weight of the composition.

3. The oral care composition of claim 1, wherein the ionic liquid is present in the oral care composition at a concentration of 15 mM to 250 mM.

4. The oral care composition of claim 1, wherein the oral care composition comprises an abrasive in an amount of less than 0.1 wt % based on the total weight of the composition.

5. The oral care composition of claim 4, wherein the oral care composition comprises an abrasive in an amount of less than 0.01 wt % based on the total weight of the composition.

6. The oral care composition of claim 1, wherein the composition is substantially free of any abrasives.

7. The oral care composition of claim 1, wherein the composition further comprises one or more agents selected from diluents, bicarbonate salts, pH modifying agents, surfactants, foam modulators, thickening agents, viscosity modifiers, sweeteners, flavorants, pigments, an antibacterial agent, anticaries agents, anticalculus agents, tartar control agents, abrasives and mixtures thereof.

8. The oral care composition of claim 1, wherein the surfactant is present in the oral care composition in an amount of 0.75 wt % to 1.5 wt % based on the total weight of the composition.

9. The oral care composition of claim 1, wherein the composition comprises glycerin, sorbitol, and propylene glycol.

10. The oral care composition of claim 9, wherein glycerin is present in an amount of 0.1 wt % to 15 wt % based on the total weight of the composition, sorbitol is present in an amount of 0.1 wt % to 20 wt % based on the total weight of the composition, and propylene glycol is present in an amount of 0.1 wt % to 7 wt % based on the total weight of the composition.

11. The oral care composition of claim 9, wherein glycerin is present in an amount of 15 wt % to 40 wt % based on the total weight of the composition, sorbitol is present in an amount of 20 wt % to 40 wt % based on the total weight of the composition, and propylene glycol is present in an amount of 10 wt % to 40 wt % based on the total weight of the composition.

12. The oral care composition of claim 7, wherein the antibacterial agent is cetyl pyridinium chloride (CPC).

13. A method of removing or reducing plaque from the oral cavity of a subject, comprising administering a therapeutically effective amount of the oral care composition according to claim 1 to the subject.

14. The oral care composition of claim 1, wherein the total amount of ionic liquid present in the composition is between 20 wt % and 40 wt % based on the total weight of the composition.

* * * * *